US008821906B2

(12) United States Patent
Deppisch et al.

(10) Patent No.: US 8,821,906 B2
(45) Date of Patent: Sep. 2, 2014

(54) BIOCOMPATIBLE POLYMER (75) Inventors: Reinhold Deppisch, Hechingen (DE);
Ruth Dietrich, Hechingen (DE);
Werner Beck, Rottenburg (DE); Andrea Schnell, Bisingen-Thanheim (DE);
Bernd Wittner, Hechingen (DE)

(73) Assignee: Gambro Lundia AB, Lund (SE)

( * ) Notice: Subject to any disclaimer, the term of this patent is extended or adjusted under 35 U.S.C. 154(b) by 804 days.

(21) Appl. No.: 10/557,996

(22) PCT Filed: May 24, 2004

(86) PCT No.: PCT/SE2004/000804
§ 371 (c)(1),
(2), (4) Date: Nov. 22, 2005

(87) PCT Pub. No.: WO2004/103425
PCT Pub. Date: Dec. 2, 2004

(65) Prior Publication Data
US 2006/0275368 A1 Dec. 7, 2006

Related U.S. Application Data (60) Provisional application No. 60/552,764, filed on Mar. 12, 2004.

(30) Foreign Application Priority Data

May 23, 2003 (SE) .................... 0301546

(51) Int. Cl.
*A01N 25/00* (2006.01)
*A61F 2/00* (2006.01)
*A61K 9/14* (2006.01)
*A01N 59/16* (2006.01)
*B32B 27/00* (2006.01)
*B32B 27/40* (2006.01)
*A01N 55/02* (2006.01)
*A61K 31/29* (2006.01)
*C08F 283/04* (2006.01)
*A61K 33/24* (2006.01)
*A61L 27/54* (2006.01)
*A61L 29/08* (2006.01)
*A61K 31/555* (2006.01)
*A61L 27/34* (2006.01)
*A61L 31/10* (2006.01)
*A61K 31/60* (2006.01)
*A61L 31/16* (2006.01)
*A61L 29/16* (2006.01)
*A61L 31/08* (2006.01)
*A61K 45/06* (2006.01)
*A61L 33/02* (2006.01)

(52) U.S. Cl.
CPC ............... *A61K 31/29* (2013.01); *A61K 33/245* (2013.01); *A61L 27/54* (2013.01); *A61L 29/085* (2013.01); *A61K 31/555* (2013.01); *A61L 2300/404* (2013.01); *A61L 27/34* (2013.01); *A61L 2300/102* (2013.01); *A61L 31/10* (2013.01); *A61K 31/60* (2013.01); *A61L 2300/624* (2013.01); *A61L 31/16* (2013.01); *A61L 29/16* (2013.01); *A61L 31/088* (2013.01); *A61K 45/06* (2013.01); *A61L 33/02* (2013.01); *A61L 2400/12* (2013.01)
USPC ........... 424/405; 424/423; 424/486; 424/653; 428/425.5; 514/503; 525/453

(58) Field of Classification Search
None
See application file for complete search history.

(56) References Cited

U.S. PATENT DOCUMENTS

| 5,256,334 | A | * | 10/1993 | Smid et al. ...................... 252/478 |
| 5,702,823 | A | | 12/1997 | Forrestal et al. |
| 5,928,671 | A | | 7/1999 | Domenico |
| 6,113,636 | A | | 9/2000 | Ogle et al. |
| 6,190,407 | B1 | | 2/2001 | Ogle et al. |
| 6,248,371 | B1 | * | 6/2001 | Domenico ...................... 424/653 |
| 6,267,782 | B1 | | 7/2001 | Ogle et al. |
| 6,506,410 | B1 | | 1/2003 | Park et al. |
| 6,866,859 | B2 | | 3/2005 | Pastecki et al. |
| 2003/0031784 | A1 | * | 2/2003 | Perrut ............................ 427/212 |
| 2003/0069629 | A1 | * | 4/2003 | Jadhav et al. ................. 623/1.15 |
| 2003/0082485 | A1 | * | 5/2003 | Bulthaup et al. .............. 430/312 |
| 2006/0275368 | A1 | | 12/2006 | Deppisch et al. |

FOREIGN PATENT DOCUMENTS

| EP | 0 294 525 B1 | 2/1993 |
| EP | 0 470 443 B1 | 4/1996 |
| EP | 1 249 232 | 7/2002 |
| GB | 1 041 058 | 9/1966 |
| JP | 2001-081263 | 3/2001 |
| JP | 2001-523527 | 11/2001 |
| JP | 2002-020269 | 1/2002 |

(Continued)

OTHER PUBLICATIONS

Tang et al. Anti-inflammatory properties of triblock siloxane copolymer-blended materials. Biomaterials 1999 20:1365-1370.*

(Continued)

*Primary Examiner* — Robert A Wax
*Assistant Examiner* — Caralynne Helm
(74) *Attorney, Agent, or Firm* — Barnes & Thornburg LLP (57) ABSTRACT The present disclosure relates to a biocompatible polymer composition for an article comprising a surface intended to contact blood, tissue, skin, epithelial layers, wounds, cells in culture fluids, body fluids, dialysis fluids, therapeutic fluids, or mixtures thereof for removal or infusion. The invention also relates to a method for the preparation of an article comprising the biocompatible polymer composition and a use thereof.

12 Claims, 2 Drawing Sheets (56) References Cited

FOREIGN PATENT DOCUMENTS

| JP | 2002-308728 |  | 10/2002 |
|---|---|---|---|
| WO | 99/26666 | A2 | 6/1999 |
| WO | WO 00/18374 |  | 4/2000 |
| WO | WO 00/21585 |  | 4/2000 |
| WO | WO 00/64506 |  | 11/2000 |
| WO | WO 02/13701 | A1 | 2/2002 |
| WO | WO 03/000303 | A1 | 1/2003 |
| WO | WO 03/047636 | A2 | 6/2003 |
| WO | WO 3082926 | A2 * | 10/2003 |

OTHER PUBLICATIONS

Arata et al. Environmental Toxicology 2002 17:472-477.*
Rawls Dental Materials 1992 8:54-59 abstract.*
R. Deppisch et al.; "Role of Proteinase/antiproteinase Inhibitor Disequilibrium in the Bioincompatibility Induced by Artificial Surfaces;" *Nephrology Dialysis Transplantation*, vol. 9, Suppl. 3, pp. 17-23 (1994).
P. Domenico et al.; "Activities of Bismuth Thiols Against Staphylococci and Staphylococcal Biofilms;" *Antimicrobial Agents and Chemotherapy*, vol. 45, No. 5, pp. 1417-1421 (2001).
P. Domenico et al.; "The Potential of Bismuth-Thiols for Treatment and Prevention of Infection;" *Infections in Medicine*, vol. 17, No. 2, pp. 123-127 (2000).
R. M. Donlan; "Biofilms and Device-Associated Infections;" *Special Issue*, vol. 7, No. 2, pp. 277-281 (2001).
K. Futschik et al.; "Electrode and Media Impedance for Detection and Characterization of Microorganisms;" *Proceedings RC IEEE-EMBS & 14th BMESI*, IEEE Catalog No. 95TH 8089, pp. 1.75-1.76 (1995).
A. J. Lovinger et al.; "Morphology and Properties of Polycaprolactone-Poly(Dimethyl Siloxane)-Polycaprolactone Triblock Copolymers;" *Journal of Polymer Science*, vol. 31, No. 2, pp. 115-123 (1993).
L. A. Mermel; "New Technologies to Prevent Intravascular Catheter-Related Bloodstream Infections;" *Special Issue*, vol. 7, No. 2, pp. 197-199 (2001).
C. Tsai et al., "Surface Modifying Additives for Improved Device-Blood Compatibility;" *ASAIO Journal*, vol. 40, No. 3, pp. M619-M624 (1994).
I. Wang et al.; "*Staphylococcus epidermidis* Adhesion to Hydrophobic Biomedical Polymer is Mediated by Platelets;" *The Journal of Infectious Diseases*, vol. 167, No. 2, pp. 329-336 (1993).
A. P. Wieslander et al.; "Toxicity of Peritoneal Dialysis Fluids on Cultured Fibroblasts, L-929;" *Kidney International*, vol. 40, pp. 77-79 (1991).
Derwent Abstract for JP 2001-081263 dated Mar. 27, 2001.
Derwent Abstract for JP 2001-523527 dated Nov. 27, 20001.
Derwent Abstract for JP 2002-020269 dated Jan. 23, 2002.
Derwent Abstract for JP 2002-308728 dated Oct. 23, 2002.
AlarmBlue® Technical Datasheet, AbD Serotec (2008).
Arata, T. et al. "Cytotoxic effects of triphenylbismuth on rat thymocytes: Comparisons with bismuth chloride and triphenyltin chloride," *Environmental Toxicology* 17(5): Abstract (1999).
BacTrac® 4300 SY-Lab Geräte GmbH, downloaded from www.sylab.com on Sep. 21, 2010.
Schindler, R. et al. "Modification of the Hemodialysis (HD) Catheter Surface Reduces Bacterial Colonization; a Randomized Controlled Trial," *Vascular Access 2*, MP357, p. ii 353 (May 12, 2008).
Schindler, R. et al. "Bismuth coating of non-tunneled haemodialysis catheters reduces bacterial colonization: a randomized controlled trial," *Nephrol. Dial. Transplant*, pp. 1-6 (2010).
Summers, WK. "Bismuth Toxicity Masquerading as Alzheimer's Dementia," *Journal of Alzheimer's Disease*, 1: 57-59 (1998).
McFarland, J. "The Nephelometer: An Instrument for Estimating the Number of Bacteria in Suspension Used for Calculating the Opsonic Index and for Vaccines," *Journal of the American Medical Association*, 14: 1176-1178 (1907).
Official action for JP 2006-500764 dated Nov. 26, 2008, with English language translation, 9 pages.

* cited by examiner

BIOCOMPATIBLE POLYMER

This application is a national stage filing under 35 U.S.C. §371 of International Application No. PCT/SE2004/000804, filed on May 24, 2004, and published in English. This application claims priority of Swedish Patent Application No. 0301546-8, filed on May 23, 2003, and the benefit of U.S. Provisional application No. 60/552,764, filed Mar. 12, 2004.

TECHNICAL FIELD OF THE INVENTION

The present invention relates to a biocompatible polymer composition for an article having a surface intended to contact blood, tissue, skin, epithelial layers, wounds, cells in culture fluids, body fluids, dialysis fluids and/or therapeutic fluids for removal or infusion.

The invention also relates to a method for the preparation thereof, an article comprising the biocompatible polymer composition and a use thereof.

BACKGROUND ART

Many of the medical devices used in contact with blood, tissue, skin, epithelial layers, wounds, cells in culture fluids, body fluids, dialysis fluids and/or therapeutic fluids for removal or infusion are made of materials which are not biocompatible. Thus in many systems the materials are creating untoward reactions in the context of application in the respective biological system. Different types of application are e.g. transcutaneous, in the peritoneal cavity, for access to the vascular system or in lines in which dialysis fluids are prepared.

Lack of biocompatibility may lead to blood clotting as well as inflammation and tissue activation and in addition, microbial infection can establish on the surface of devices. Colonization of bacteria and formation of biofilms on surfaces is a basic medical problem. Devices intended for long term contact, e. g. such as implanted stents, body fluid drainage systems or indwelling catheters can serve as a surface for host cell adhesion, permitting host cells to become activated, proliferate or to alter the normal physiological function and to restrict the function or intended use of a device. The formation of biofilms or bacteria colonisation on medical device surfaces creates a chronic inflammatory situation, which finally initiates failure of the device, and severe medical interventions or even life threatening situations.

The importance of antimicrobial activity and prevention of clot formation, e. g. in a catheter, has been disclosed in a paper by Wang et al, "*Staphylococcus Epidermis* Adhesion to Hydrophobic Biomedical Polymer is Medicated by Platelets", J. of Infectious Diseases, 1993, 167:329-36, where a strong relation is described between platelets deposition and promotion of bacterial growth.

GB-1 041 058 discloses a composition and a method for protecting materials against attack by fungi or bacteria, wherein a bismuth compound is applied to a surface, e.g. by spraying or tipping, or is incorporated into the material which is to be protected during fabrication thereof. The bismuth compound is used in applications with textiles, paintings, and disinfectant or to protect plants against attack by fungi and other microorganisms.

In U.S. Pat. No. 5,928,671 is disclosed a series of bismuth salts having bactericidal and bacteriostatic activity for pharmacological use, antiseptic, antimicrobial and antibacterial agents for preventing infection and for disinfecting and cleaning surfaces, preservative and for killing biofilm organism and preventing the formation of biofilm. The composition is also used for treating bacterial infections of the gastro-intestinal tract.

A series of bismuth complexes, e. g. bismuth-propanedithiol or bismuth-pyrridione having antimicrobial and biofilm inhibition properties, have been described by Domenico et al, "The potential of bismuth-thiols for treatment and prevention of infection", Infect. Med., 17(2):123-127, 2000. Said complexes are proposed to be used for coating of, e. g. indwelling catheters. Furthermore, Domenico et al have discussed the "Activities of bismuth thiols against Staphylococci and Staphylococcal biofilms", Antimicrobial Agents and Chemotherapy, May 2001, p. 1417-1421.

WO 00/21585 discloses polycaprolactone, PDMS, as part of a polymeric film by the addition of a further component exerting antimicrobial activity and keeping the high biocompatibility profile of the coating (no cytotoxicity, improved thrombogenicity and reduced promotion of bacterial growth).

U.S. Pat. No. 6,267,782 relates to a mixture of a metal composition and a biocompatible material in a solution for the preparation of a medical article comprising antimicrobial metal. The biocompatible material may comprise a biological polymer and the metal may be a bismuth composition. However, the metal composition is deposited on the surface of the article, resulting in release of bismuth from the article.

Prevention of blood access derived infections, e. g. in catheters is of great importance in public health perspectives, i. e. increasing resistance of bacteria against antibiotic strategies and with respect to costs related to subsequent medical treatment after bloodstream infections and septic complications. For example, intravascular catheter related bloodstream infections are an important cause of illness and excessive medical costs. Many catheter related bloodstream infections occur in intensive care units at the price of many deaths and high cost.

Therefore a lot of strategies have been developed to prevent these complications. As described by Donlan et al, "Biofilms and Device-associated Infections, Emerging Infectious Diseases, 89, Vol. 7, No. 2, March-April, 2001, most of these strategies to impregnate polymeric materials, e g by silver or other additives or even antibiotics, result in an ineffective control of bacteria growth and biofilm formation.

It is described by Mermel et al, "New Technologies to Prevent Intravascular Catheter Related Bloodstream Infections", Emerging Infectious Diseases, Vol. 7, No. 2, March-April, 2001, that technological interventions by impregnating catheter materials with different kinds of bacterial agents is not effective. In vitro studies have suggested the potential for bacterial resistance against the antimicrobial agents used to impregnate these catheters as their clinical use becomes more widespread. In addition to these very often non-technological inventions such as nurse training and use of sterile environment by sterile masks, sterile clothes, etc helps to reduce catheter related infections.

However, there is no technical solution available at the moment preventing, at the catheter site, the formation of biofilms by bacterial adhesion and proliferation. From pharmaceutical textbook knowledge, many bismuth compounds are used in medical and/or pharmaceutical practice e g bismuth carbonate, bismuth-nitrate, bismuth-citrate, bismuth-salicylate. Related drug formulations are known as Angass-S-Ulcowics, Bismoflk-V, Jadrox-600, Ulcolind, etc. Bismuth salts and thiols are active against a broad spectrum of bacteria. The inhibitory concentration is in the range of 3 to 300 µmol bismuth-3+. Most of the known bacteria strains are susceptible to bismuth compounds and it is of importance to note that they are most effective against *Staphylococcus Aureus* including methicillin resistant *Staph. aureus* (MRSA) (Dominico et al).

The main problem is that bismuth compounds, especially bismuth thiols are potentially toxic. The mechanism how bismuth is working to prevent bacterial proliferation is not completely clear. It was recently shown that Bis-BAL could enhance phagocytotic uptake of bacteria by neutrophils. Furthermore it has been shown that this compound could significantly enhance complement binding to cells and by this accelerate opsonisation and phagocytosis. However, this mechanism cannot be applied to prevent bacterial growth in aqueous solution. Therefore, a specific effect of bismuth must act on bacteria proliferation. It has been proposed that bismuth inactivates respiratory enzymes in the cytoplasma and by this leads to inhibition of capsular polysaccharide expression in bacteria. These polysaccharides are necessary to form a gel like autolayer surrounding the bacteria and preventing the action of antibiotic. Furthermore, it is advantageous that bismuth does not destroy the bacterial cell membrane and by this prevents the release of endotoxins which are known as an important stimulator of the immune system, especially in dialysis patients or patients depending on extracorporeal treatment during intensive care therapies.

Based on these findings, there is a clear medical need to design materials or surfaces in medical devices, especially in catheters, access devices or port systems, which prevent bacterial growth and subsequent biofilm formation and prevent bioincompatible reactions, especially formation of clots and fibrin or platelets deposits. To produce medical devices resistant to infections, a potent antimicrobial efficiency combined with an excellent biocompatibility over time is needed.

SUMMARY OF THE INVENTION

The object of the present invention is to provide a biocompatible polymer composition for an article having a surface intended to contact blood, tissue, skin, epithelial layers, wounds, cells in culture fluids, body fluids, dialysis fluids and/or therapeutic fluids for removal or infusion, wherein the above mentioned drawbacks and problems have been eliminated or at least alleviated.

Thus, it is an object of the present invention to provide a biocompatible polymer composition capable of preventing bacterial adhesion and proliferation including biofilm formation.

This object has been achieved by the biocompatible polymer composition for an article having a surface intended to contact blood, tissue, skin, epithelial layers, wounds, cells in culture fluids, body fluids, dialysis fluids and/or therapeutic fluids for removal or infusion, characterized in that the polymer composition comprises a bismuth complex is incorporated in an amount corresponding to 0.001-0.5 weight % bismuth, more preferably 0.001-0.1 weight % bismuth and most preferably 0.002 to 0.08 weight % bismuth of the polymer composition.

Another object of the present invention is to provide a method for the preparation of the biocompatible polymer composition.

This object has been achieved by a method for the preparation of a biocompatible copolymer composition, characterized in that a bismuth complex is incorporated into the polymer composition in an amount corresponding to 0.001-0.50 weight % bismuth, preferably 0.002 to 0.08 weight % bismuth of the polymer composition.

Yet another object according to the invention is to provide an article having a surface intended to contact blood, tissue, skin, epithelial layers, wounds, cells in culture fluids, body fluids, dialysis fluids and/or therapeutic fluids for removal or infusion.

This object has been achieved by an article, characterized in that said article has a film of a polymer composition comprising a bismuth complex in an amount corresponding to 0.001-0.5 weight % bismuth, more preferably 0.001-0.1 weight % bismuth and most preferably 0.002 to 0.08 weight % bismuth of the polymer composition, covering said surface.

A further object of the invention is to provide a use of a biocompatible polymer composition.

This object has been achieved by the use of a biocompatible polymer composition comprising a bismuth complex incorporated into the polymer composition, for a medical device intended to contact blood, tissue, skin, epithelial layers, wounds, cells in culture fluids, body fluids, dialysis fluids and/or therapeutic fluids for removal or infusion in order to enhance biocompatibility and prevent bacterial growth. The biocompatible polymer of the invention may e.g. be used on surfaces in contact with blood, tissue, skin, epithelial layers, wounds, cells in culture fluids, body fluids, dialysis fluids and/or therapeutic fluids for removal or infusion.

According to an illustrative embodiment of the invention, the film-forming polymer of a biocompatible polymer composition is a polyurethane and the hydrophobic polymer block is a polylactone-polysiloxane-polylactone triblock copolymer containing mono, bi or multiple reactive end groups.

According to an illustrative embodiment of the invention, the film-forming polymer used in a method for the preparation of a biocompatible copolymer composition is a polyurethane, and the hydrophobic polymer block is a polylactone-polysiloxane-polylactone triblock copolymer containing mono, bi or multiple reactive endgroups.

According to an illustrative embodiment of the invention, the film-forming polymer of an article having a surface intended to contact blood, tissue, skin, epithelial layers, wounds, cells in culture fluids, body fluids, dialysis fluids and/or therapeutic fluids for removal or infusion is a polyurethane and the hydrophobic polymer block is a polylactone-polysiloxane-polylactone triblock copolymer containing mono, bi or multiple reactive endgroups.

The present invention shows a possibility to create antimicrobial biocompatible polymer compositions for any medical devices by means of bismuth components in polymer systems.

Another advantage of the invention is that the addition of Bi influences the polymer film composition and orientation of physicochemical domains in the surface, e.g. by catalysing the polymer forming reaction and thus allowing different functions.

Other distinguishing features and advantages of the invention will appear from the following specification and the appended claims.

A specific advantage derives from the process of coating/reactive polymer film making on a medical device containing an active compound in the thin crosslinked polymer layer. The ratio of base polymer substratum against the thickness of the polymeric film coating defines important properties of the medical article related to general function, biocompatibility and antimicrobial activity.

SHORT DESCRIPTION OF THE DRAWINGS

The invention will be described in greater detail below by means of the accompanying drawings, wherein.

DETAILED DESCRIPTION OF PREFERRED EMBODIMENTS

Figure 1:
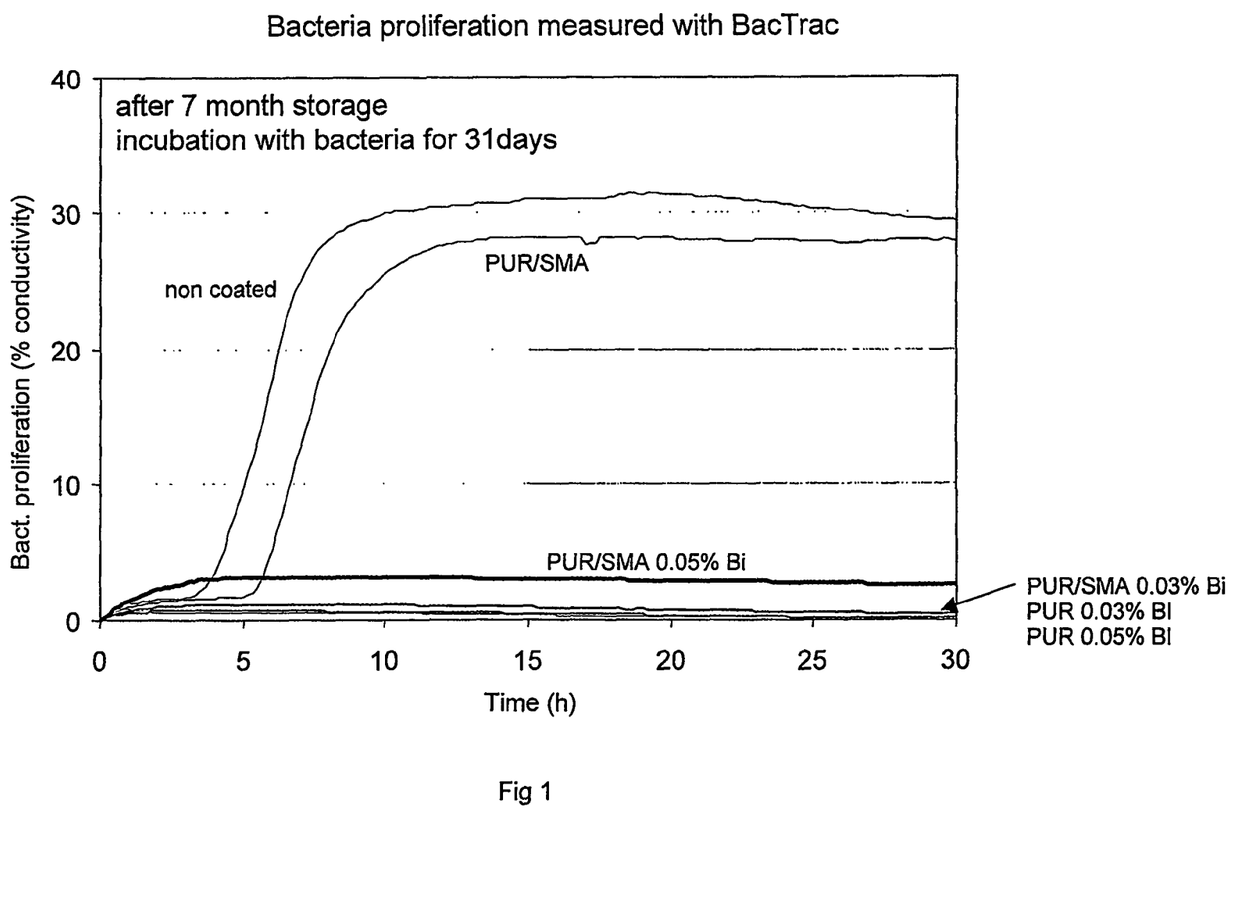
FIG. 1 is a graph of bacteria proliferation for an article coated by PUR/SMA with 0.03% Bi incorporated therein versus a non-coated article.
Figure 2:
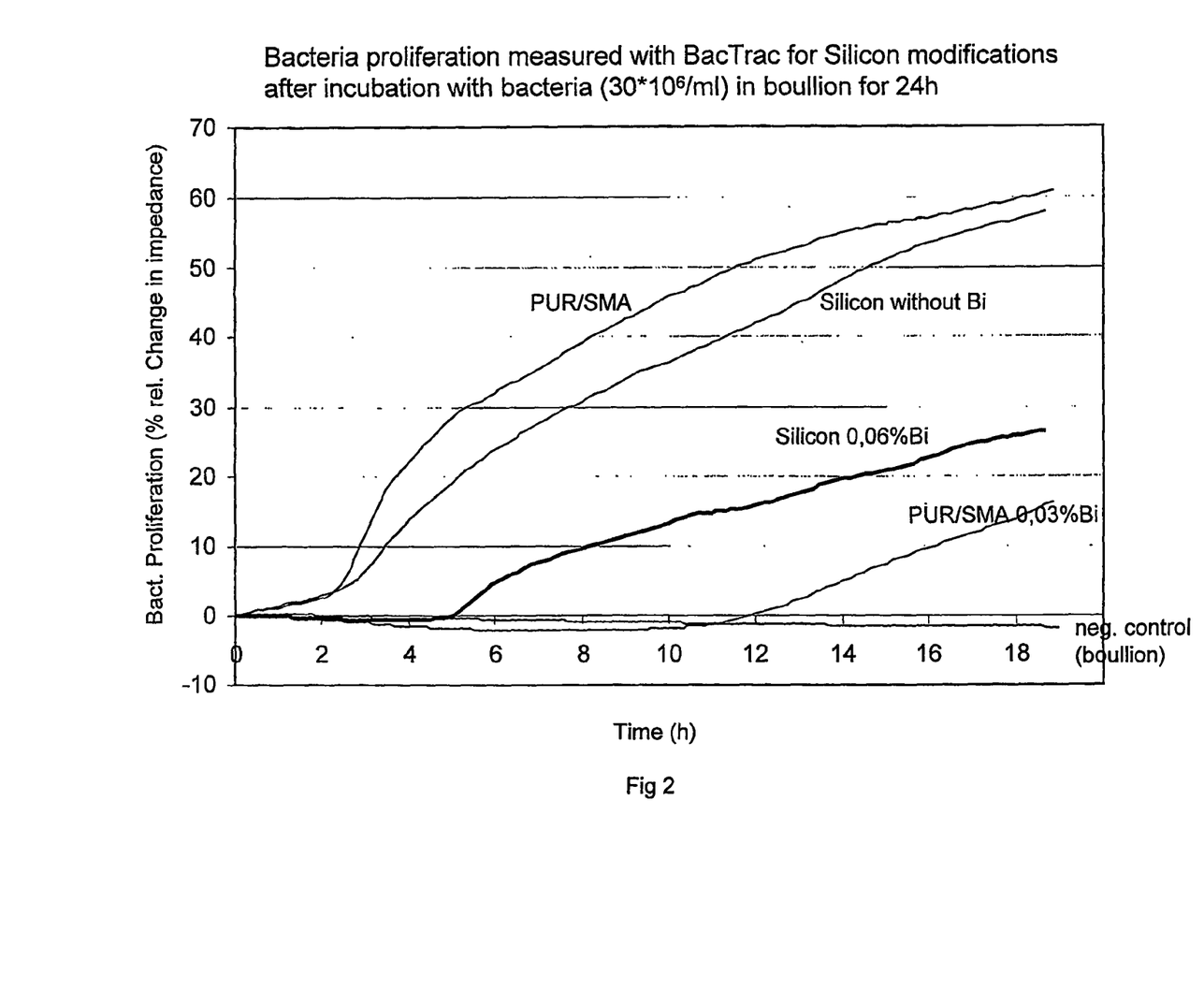
FIG. 2 is a graph of bacteria proliferation for a silicon article with 0.06% Bi incorporated therein versus a non-coated silicon article, an article coated by PUR/SMA with 0.03% Bi incorporated therein and a non-coated article.

The present invention includes a polymer composition, which can be applied as a film over a surface of an article to form a continuous surface which is more biocompatible and has a smoother surface morphology than an untreated article. Such polymer film can be formed by providing a hydrophobic polymer block, such as polydimethylsiloxane (PDMS) with two or more functional —OH end groups and reacting the —OH ends with a conventional monomer or prepolymer of a film-forming polymer capable of reacting with —OH groups. Such reactions are exemplified, using as reactive PDMS a triblock copolymer of the polylactone-polysiloxane-polylactone (PL-PDMS-PL) type or silicone polyesters. The —OH groups of the polylactone blocks can react with any of a variety of isocyanates in a suitable solvent to form a polymer having PDMS incorporated with its structure. The film can be applied to the surface of an article by any convenient means of coating the article with the reaction mixture in solvent, and allowing the solvent to evaporate.

The copolymer film can be prepared by reaction of a hydrophobic polymer block, for example a PDMS-containing block copolymer having reactive —OH groups, with a monomer or prepolymer of a film-forming polymer, for example, an isocyanate-polyol mixture. Suitable hydrophobic polymer blocks include various siloxane polymers, siloxane oligomers, fluoropolymers, polyethyleneglycols, polyethyleneglycol polydimethylsiloxane copolymers, silicone polyesters, polylactone-polysiloxane-polylactone triblock copolymers, polyamides, polysulfones, polyarylethersulfone, polycarbonates, polyolefins including cycloolefine-copolymers and the like. Basically all kinds of block copolymers can be applied for coating films according to the described invention. Reactive end groups on the hydrophobic polymer block react with monomer or prepolymer units of the film forming polymer. Alternatively, coupling agents can be used to react with the hydrophobic block and then with monomer or prepolymer units of the film-forming polymer.

Examples of film-forming polymers include polyurethanes, polyolefins, elastomers, polyethyleneglycols, polycarbonates, polyethersulphones, polyvinyl pyrrolidones, polyvinyl chlorides, polyamides, polysulfones, polyarylethersulfones, cellulosic polymers, cycloolefin-copolymers, siloxane polymers and siloxane oligomers, and the like. Preferred are polyurethanes (PUR), which can be formed by reaction of isocyanate with a polyol. PL-PDMS-PL has —OH groups, which allow it to be incorporated internally into a polyurethane by reaction with free isocyanate groups. In order to create more or multiple dimensional crosslinking of the PUR system PDMS-polymers or copolymers with more than two OH groups can be applied. One example of oligomers of this type is disclosed in EP 0 294 525, which is hereby included by reference.

In a preferred embodiment of the present invention the polymer composition contains polyisocyanate-prepolymer with a NCO-content of 1-60% which is reacted with a OH-group of a polymer containing hydrophobic domains such as triblock-copolymer of polycaprolactone-polydimethyl-siloxane-polycaprolactone of molecular weight in the range 100-100,000.

Triblock copolymers having a polydimethyl siloxane (PDMS) block flanked by polylactone (PL) blocks have been described by Lovinger, J. et al (1993), J. Polymer Sci. Part B. (Polymer Physics) 31:115-123. Such triblock copolymers have been incorporated into bulk formulations, and also applied as surface coatings, to reduce thrombogenicity, as described in U.S. Pat. No. 5,702,823. PL-PDMS-PL triblock copolymers are commercially available, for example from Thoratec Laboratories, Berkley, Calif., which provides a series of such polymers designated SMA in which the siloxane is dimethyl siloxane and the lactone is caprolactone, and from Th. Goldsmith AG, Essen, Germany, under the name TEGOMER (trademark, Goldsmith AG). The nominal molecular weights (number average) of the polysiloxane blocks suitable for use herein range from about 1000-5000, while the nominal molecular weights of the caprolactone blocks range from about 1000 to about 10,000. Tsai, C-C. et al (1994) ASAIO Journal 40:M619-M824, reported comparative studies with PL-PDMS-PL blended into polyvinyl chloride and other base polymers or applied as a coating thereon.

In this reactive mixture bismuth containing salts, thioles or other bismuth-complexes are added to form a mechanically stable film which can react in presence of humid air to accelerate the polymer forming reaction. The concentration of the bismuth complexes should be in the range corresponding to 0.001-0.5 weight % bismuth, more preferably 0.001-0.1 weight % bismuth and most preferably 0.002 to 0.08 weight % bismuth of the polymer composition.

The bismuth complexes may be accumulated in the outer layer of the film. Without being bound to any theory it is suggested that the bismuth complexes could migrate in a direction away from the film surface in order to accomplish equalization of the concentration of bismuth complexes throughout the film. In order to prevent this, in a preferred embodiment of the invention, nano-particles including a bismuth complex are further added to the polymer composition as a complement in order to achieve a slow-release of bismuth complex. By the presence of nano-particles containing bismuth complex it is possible to delay depletion of bismuth complex from the polymer film surface. The nano-particles may be prepared from polylactic acid. By controlling the degree of polymerisation of the polylactic acid it is possible to control the rate of the release of bismuth from the nano-particles.

In another preferred embodiment of the invention a catheter is provided with a first film with nano-particles having slow-release of bismuth complex incorporated therein. Subsequently a second film is provided with free bismuth complexes. The slow release of bismuth complexes from the first film then prevents the migration of the free bismuth complexes in a direction away from the film surface, inwards into the polymer film.

The invention also provides a method of coating an article with a polymer film, by combining a film-forming polymer composition and a bismuth complex with a hydrophobic polymer block having end groups reactive with the film-forming polymer component in the presence of a solvent such that all components are dissolved in the solvent. Subsequently, the components dissolved in the solvent are incubated under conditions to allow the components to react with one another in solution. Finally, a film is formed by spreading the solution over a surface to be coated under conditions that allow the solvent to evaporate.

More than one film may be formed on the surface to be coated. It is also possible for the different film layers to have different thickness. Furthermore, the concentration of bismuth in the different layers may also vary. In this way it is possible to achieve a desired distribution profile for the bismuth complex. The thickness of the films may be in the range from about 1-100 μm, preferably in the range from about 5-50 μm.

The invention is carried out by using a commercially available PL-PDMS-PL, a triblock copolymer of poly-caprolactone-polydimethylsiloxane-polycaprolactone such as TEGOMER H—Si 6440 (trademark, Th. Goldsmith A. G., Essen, Germany,) and adding a bismuth containing salt, thiol or other bismuth complex thereto.

In an alternative embodiment the invention is carried out by using siloxane polymers and/or siloxane oligomers with the addition of a bismuth complex.

Examples of suitable bismuth complex are chosen from the group comprising ammonium bismuth citrate, bismuth(III) oxide, bismuth(III)gallate hydrate, bismuth citrate, bismuth (III)oxychloride, bismuth(III)tetramethylheptanedionate, bismuth(III)hexafluoracetonate, bismuth(III)subsalicylate, triphenylbismuth, bismuth(III)ciprofloxacin, bismuth(III) chloride, triphenylbismuth dichloride, triphenylbismuth carbonate, triphenylbismuth dihydroxide, triphenylbismuth dinitrate, triphenylbismuth disalicylate, triphenylbismuthine, triphenylbismuth bis(2-chloroacetate), triphenylbismuth bis (4-aminobenzoate), bis(acetato-O)triphenylbismuth, dibromotriphenylbismuth, and difluorotriphenylbismuth. Bismuth thiols such as bismuth propanedithiol, bismuth pyrithione and bismuth dimercaptotoluene, etc, may also be used. The concentration of the bismuth complexes should be in the range corresponding to 0.001-0.5 weight % bismuth, more preferably 0.001-0.1 weight % bismuth and most preferably 0.002-0.08 weight % bismuth. In a preferred embodiment of the invention the bismuth complex is triphenylbismuth or triphenylbismuth dichloride.

Subsequently, the Bi-containing PL-PDMS-PL triblock copolymer is reacted with a polyurethane (PUR) prepolymer (DESDOMUR E23, Trademark, Bayer Co.), wherein PL-PDMS-PL blocks react as bifunctional units that become incorporated internally in the PUR polymer chain.

The —NCO content should be within the range of 1-60 weight %, more preferably 5-20 weight % and most preferably 7-16 weight %.

The formulation is used to prepare, e. g. a film or a coating or a surface which film or coating is chemically crosslinked, mechanically stable, elastic, non-toxic, exerts inhibition of bacteria growth in comparison with films or coatings without bismuth complexes and reduced thrombogenicity in comparison with uncoated surfaces.

Alternatively a Bi-complex may be added as an additive in injection moulded parts. Other technical processes like casting or extrusion of films, plates or multilayer tubular materials are suitable to create the described polymer film on a surface. Another possibility is to create the polymer film by a spraying, etc.

The biocompatible polymer composition according to the invention is ideally used for a medical device intended to contact blood, tissue, skin, epithelial layers, wounds, cells in culture fluids, body fluids, dialysis fluids and/or therapeutic fluids for removal or infusion in order to enhance biocompatibility and prevent bacterial growth, preferably a catheter to get transcutaneous access to the body of a patient including peritoneal catheter including patient extension lines, transcutaneous tunnels, e g cuffs, but it could also be used in a dialysis monitor wherein the composition may be used to coat the lines wherein the dialysis fluid is generated. Other fields of application are infusions therapy, implantation technology, intravenous nutrition, urethral catheter, etc.

Further, it is also possible to advantageously use the disclosed invention in any technical system, e.g. water processing systems, water pipe systems, in air filters, in membrane based separation systems to prevent fouling process, in biosensors, wound dressing or wound coverage substrate media, bioreactors, in food processing systems where biofilm formation should be prevented and biocompatibility and non-toxicity is of critical importance. Other fields of application where the described properties have obvious advantageous are sanitary products, skin or food care products including wound dressing, surgical instruments, endoscopes, textiles, hygiene articles, such as toothbrushes, wound care products, plasters, tamponates, stoma bags, storage containers, refrigerators (e.g. for storage of drugs, medical products or food) etc.

The present invention will now be illustrated by way of non-limiting examples of preferred embodiments in order to further facilitate the understanding of the invention.

EXAMPLES

Example 1

Film Preparation

Step 1:
60 g Methylisobutylketone.
5 g TEGOMER H—Si 6440 (Goldschmidt A. G.)
Warm up to 50° C. under light stirring for approximately 5 min.
TEGOMER H—Si 6440 is a triblock copolymer of poly-caprolactone-polydimethylsiloxane-polycaprolactone blocks having nominal molecular weights of 2000, 2000 and 2000, respectively.

Step 2:
Add 0.01-0.32 g triphenylbismuth dichloride (511.21 g/mol) (Aldrich), corresponding to 0.004-0.13 g bismuth.
Light stirring at room temperature for approximately 5 min.

Step 3:
Add 35 g DESDOMUR E23 (Bayer Co.).
Light stirring to avoid air bubble formation.
Degassing is required to remove air bubbles.
DESMODUR E23 is a polyisocyanate prepolymer based on diphenyl methane diisocyanate. The —NCO content is 15.4 weight %. Equivalent weight is 273.

Step 4:
a) Casting a film in various thickness on glass plate with or without support foil, e. g. PE (polyethylene or injection moulded plates made from polyurethane); or
b) Film forming by transporting solution outside and through catheter tubes (ID 1-3 mm or any other geometry).
The polymerised film was then examined by scanning electron microscopy.

Example 2

Testing/Assessing Thrombogenicity

PUR plates and films with or without triphenylbismuth dichloride (the ones with triphenylbismuth dichloride is the same as is described in example 1) were tested for thrombogenicity assessment using freshly donated human blood. During contact of blood components with the material the kinetic generation of thrombin-anti-thrombin III complex (TAT) was analysed as an indicator of thrombin formation. Thrombin is the major component in the coagulation circuit, since thrombin is a potent activator for platelets and cleaves fibrinogen to fibrin which finally leads to a polymerised fibrin network, i. e. a clot. TAT was measured by a commercially available ELISA test according to the instruction of the manufacturer (Behring Co., Germany). The comparison of materials/surfaces is done in direct comparison of the modified versus the non-modified polymer system. Accelerated reaction kinetics for TAT indicates less biocompatible, more thrombogenic material.

For details on methodology for thrombogenicity assessment: Deppisch R. et al (1993) Nephrol. Dial. Transplant Supp. 3 (1994) 17-23 and Tsai et al (1994) ASAIO J. 40:M619-M624.

In vitro analysis was performed with freshly donated human whole blood. TAT data after 40 min blood contact for TEGOMER-PUR-Bi films prepared according to Example 1 are shown in table 1.

TABLE 1

TAT values after 40 min activation with human whole blood

| Material | TAT[µg/l] |
|---|---|
| Uncoated plate PUR(Tecoflex) | 363 |
| Film PUR —TEGOMER | 210 |
| Film PUR —TEGOMER-0.03% Bi | 224 |
| Positive control | >2000 |

Data depicted in table 1 show that films on surfaces result in reduction of thrombin formation in whole blood compared to non-treated standard PUR surfaces (polyurethane formulation by Thermedics Co., Tecoflex®, is standard polymer material in hemodialysis catheters). There is no negative influence by adding the bismuth complex triphenylbismuth dichloride compared to films without bismuth complex. These experiments were performed versus a positive control which is polystyrene (as used in Greiner tissue culture plates) resulting in a TAT formation of >2000 µg/l.

Example 3

Cell Toxicity Studies

The toxicity of various combinations of film coatings prepared according to example 1 was evaluated by measuring inhibition of cell growth (ICG). ICG was measured by making aqueous eluates of the various test materials, then incubating growing mammalian cells in culture medium containing the eluate, and then evaluating the cell viability by neutral red uptake.

The ICG test was begun by seeding a 96-well tissue culture plate with 1500-2000 mouse fibroblast cells (strain L-929) previously grown to subconfluence for 48-72 h in complete Eagles MEM (minimal essential media as described in text books for cell culture). The plates were incubated for 24 h at 37° C. The medium was then removed and test eluates were added and incubated. The test eluates were made by incubating test plates or films in distilled water (1 ml for each 10 cm² test material) at 70° C. for 24 h.

For each plate, 250 µl 0.4% neutral red solution was mixed with 20 ml of complete Eagle's MEM. The eluate incubation medium was removed and 200 µl/well of neutral red containing medium was added. The plates were then incubated for 3 h at 37° C. The solution was then discarded, the plates rinsed with 200 µl PBS/well. After that, 200 µl/well of 50% (v/v) ethanol and 1% (v/v) acetic acid in distilled water was added. After a 10 min wait the absorbance at 540 nm of each well was measured. ICG % was calculated as $(A_k-A_T)/A_k \times 100$, where $A_T$=mean absorbance in test solution minus mean absorbance in blank. The materials are deemed non-toxic if ICG is <30%, as described by Wieslander et al (1991) Kidney International 49:77.79.

The following materials were employed:
Completed Eagles MEM:
    500 ml Eagles MEM
    50 ml Fetal calf serum
    5 ml 200 m ML-Glutamine
    5 ml Non-Essential Amino Acid solution
    0.5 ml Gentamycin 50 mg/ml

| PBS (10xstock solution) | |
|---|---|
| NaCl | 80 g |
| KCL | 2 g |
| $KH_2PO_4$ | 2 g |
| $Na_2HPO_4.H_2O$ | 11 g |

Dissolve in $H_2O$ to 1000 ml final volume.
The stock solution is diluted 10-fold and pH adjusted to 7.2
50% ethanol, 1% acetic acid solution:
    500 ml ethanol (96%)
    490 ml water
    10 ml Glacial acetic acid
4% Neutral red stock solution:
    4 g Neutral red (Merck No. 1376)
    100 ml distilled water
    Diluted 10-fold with water prior to use.

The results of the investigated films (prepared according to Example 1) are shown in Table 2.

TABLE 2

ICG levels of PUR films (example 1)

| Film | ICG (%) |
|---|---|
| PUR | 5 |
| PUR-TEGOMER | 3 |
| PUR-TEGOMER-0.03% Bi | 3 |
| PUR-TEGOMER-0.08% Bi | 2 |
| PUR-TEGOMER-0.24% Bi | 97 |
| PUR-TEGOMER-0.32% Bi | 92 |

Films (5-20 µm thick) with a triphenylbismuth dichloride concentration of up to 0.2 weight %, corresponding to 0.08 weight % bismuth were non-toxic in ICG assay. Films with 0.6 weight % triphenylbismuth dichloride, corresponding to 0.24 weight % bismuth and more were toxic.

As depicted in the table, inhibition of cell growth can only be seen in concentrations of bismuth >0.2%. These results together with the thrombogenicity show that bismuth as an additive component for the polyurethane PL-PDMS-PL formulation has an effect on reduced formation of thrombin and no toxicity in low concentrations (<0.08% Bi). This could lead to a reduced risk for thrombus formation and clot deposits in clinical circumstances and by this advantageously address or limit the related events of clotting followed by bacterial growth or vice versa, as it is known that clot layers, i.e.—fibrin net work with entrapped platelets or other blood cells, provide a good substrate for bacteria adhesion and biofilm development.

Example 4

Bacterial Adhesion

Bacterial adhesion was tested by two different methodologies, with the MTT assay and by scanning electron microscopy of bacterial growth. The MTT test is a rapid and sensitive calorimetric assay based on the formation of a coloured insoluble formazan salt. The amount of formazan produced is directly proportional to the cell number and therefore can be used to measure cell viability and proliferation. The assay is based on the capacity of the mitochondrial dehydrogenase enzymes to convert yellow water-soluble tetrazolium salt (=MTT) into a purple insoluble formazan product by a reduction reaction. These insoluble crystals are dissolved in DMSO and the absorbance is read with a spectrophotometer at 550-570 nm.

The MTT test was begun by seeding a concentration of $10^5$/ml of *Staphylococcus epidermidis* (ATCC 12228) in a trypcase-soja bouillon into a 24-well plates with different films and were incubated in 4 h, 8 h, 24 h, 48 h, at 37° C. After incubation the bouillon was removed and the plates were washed with PBS-buffer. Then 500 μl/well MTT solution (0.5 mg/ml in PBS) was added and incubated for another 30 minutes at 37° C. The solution was removed and 500 μl/well lysis solution (99.4 ml DMSO; 0.6 ml 100% glacial acetic acid; 10 g SDS) was added. After 10 min incubation on microtiter shaker the solution was pipetted into a 96-well plate and the absorbance was measured at 55 nm (against reference of 620 nm)

The following materials were employed:
*Staphyloccus epidermis* ATCC 12228
Plate-count-agar
Trypcase-soja bouillon
PBS buffer: 8.0 g NaCl
   0.2 g KCl
   1.44 g Na2HPO4×2 H2O
   0.2 g KH2PO4
dissolve in 1000 ml distilled water; pH 7.2
MTT solution (0.5 mg/ml in PBS)
Lysis solution (99.4 ml DMSO; 0.6 ml glacial acetic acid; 10 g SDS)

It could be clearly shown that the addition of a bismuth complex in the polymer formulation leads to complete inhibition of bacteria proliferation as measured by MTT (Table 3). It is most important that addition of bismuth in low concentration, e g non-toxic, for example 0.03%, the inhibition of bacteria proliferation cannot be correlated with the cytotoxicity of extracts.

TABLE 3

Results of the MTT test
(mean value of two experiments)
Extinction (nm)

|  | 24 h | 48 h | 72 h |
| --- | --- | --- | --- |
| Catheter material (Tecoflex) | 0.39 | 0.51 | 0.36 |
| Film PUR | 0.47 | 0.1 | 0.34 |
| Film PUR-TEGOMER | 0.40 | 0.38 | 0.29 |
| Film PUR-0.32% Bi | 0 | 0 |  |

TABLE 3-continued

Results of the MTT test
(mean value of two experiments)
Extinction (nm)

|  | 24 h | 48 h | 72 h |
| --- | --- | --- | --- |
| Film PUR-TEGOMER-0.32% Bi | 0 | 0 |  |
| Film PUR-TEGOMER-0.08% Bi | 0 | 0 |  |
| Film PUR-TEGOMER-0.03% Bi | 0 | 0 |  |

By another method electron microscopy of bacterial growth on bismuth containing PL-PDMS-PL PUR-polymeric films was performed. By these experiments it can be clearly confirmed that no bacterial growth could be detected on the Bi modified surfaces over a period of time of 32 h. No bacteria colonization or biofilm formation occurred.

Example 5

Bismuth Surface Concentration (XPS)

In order to assess the presence of bismuth on the surface x-ray fluorescence spectroscopy (XPS) was applied. Results for films prepared as in example 1 were received for different take-off angles (TOA), 10° and 90°. The greater the take off angle the higher the penetration depth for this analysis. The data show that bismuth can be detected on the surface of the films containing triphenylbismuth dichloride. The concentration is close to the detection limit of bismuth with XPS.

TABLE 4

Bismuth concentration/atom (%)
on the surface measured by XPS.

| Film | Bismuth atom (%) TOA 90° | Bismuth atom(%) TOA 10° |
| --- | --- | --- |
| PUR-TEGOMER | <0.001 | <0.001 |
| PUR-TEGOMER-0.08% Bi | 0.006 | 0.006 |
| PUR-TEGOMER-0.32% Bi | 0.02 | 0.02 |
| PUR-0.32% Bi | 0.01 | 0.02 |

To further characterize the materials of the invention analyses of bismuth surface concentrations were performed on the polymeric films. In films containing 0.08% bismuth 0.006 atom % was discovered on the surface. This should be the maximum concentration active in preventing bacteria growth and biofilm formation. This bismuth concentration is extremely low and even so surprisingly effective.

Example 7

Bismuth in Aqueous Eluate

The films were further characterized by their ability to release bismuth, see table. It could be shown that these films release in aqueous environment 0.02 mg/l extraction fluid which is below 0.05% of the total amount of bismuth given to the polymer formulation used for 600 cm² bismuth containing polymer film.

TABLE 5

Bismuth concentration in aqueous eluates

| Eluates of Films (5–20 μm) | Bi [mg/l] |
|---|---|
| PUR-TEGOMER | 0 |
| PUR-TEGOMER-0.03% Bi | 0.02 |
| PUR-TEGOMER-0.05% Bi | 0.03 |
| PUR-TEGOMER-0.08% Bi | 0.03 |
| PUR-TEGOMER-0.24% Bi | 0.19 |

Example 8

Bismuth after Extraction with Human Whole Blood

Coated catheters were tested by their ability to release bismuth in human blood. Therefore 50 ml citrated/heparinised whole blood were used for the extraction of each catheter. The extraction was made by 6 h recirculation and 24 h in the incubator to simulate a cycle of treatment period and inter-treatment intravascular position. For measurement the samples were treated with nitric acid to release Bi from the blood component matrix and measured with AAS within the precision of the analytic tools. The measurable amount of bismuth in whole blood was almost the same for bismuth-SMA coated catheters (mean values of 3 catheters) as for standard catheter (without coating). There is no enrichment of bismuth measurable in blood.

TABLE 6

Whole blood bismuth concentration after extraction

| Catheter | After 0 h Bi (mg/l) | After 6 h recirculation, 37° C. Bismuth mg/ml |
|---|---|---|
| Control(whole blood after blood donation) | 0.005 | |
| PUR (Tecoflex) non-coated catheter | | 0.015 |
| PUR-Tegomer-0.03% Bi coating (mean of 3 catheters) | | 0.014 |

Example 9

Film Preparation

Step 1:
  80 g Methylisobutylketone
  20 g Silicon MED 1011 (Nusil, Polytec GmbH)
  Mixing under light stirring at room temperature for app. 20 min. MED-1011 is a one component, self leveling silicone.
Step 2:
  Add 0.03 g triphenylbismuth dichloride (511.21 g/mol) (Aldrich) corresponding to 0.01 g bismuth. Light stirring at room temperature for app. 10 min.
  a. Casting a film on a glass plate with support foil e.g. polyethylene
  b. Film forming by transporting the solution outside and through a silicon catheter tube
  The film was examined by scanning electron microscopy.

Example 10

Bacterial Adhesion

Bacterial adhesion and proliferation was measured with the BacTrac System (Sy-Lab GmbH, Austria). With this impedance method the change of ionic composition of the nutrient media caused by the microbial metabolism is used as parameter wherein the sum of all metabolism outputs is continuously detected. The change in impedance correlates with amount of proliferating bacteria on the sample.

This method is described by Futschik et al (1995): Electrode and Media Impedance for the Detection and Characterisation of Microorganisms. Proceedings RC IEEE-EMBS & 14th BMESI, 1.75-1.76.

For measurement of bacterial adhesion and proliferation films prepared as in Example 9 were incubated with a concentration of $30*10^6$ Staphylococcus epidermidis in a trypcase-soja bouillon for 24 h hours at 37° C.

Subsequently, the pre-incubated films were transferred into the measuring cell of the BacTrac system filled with fresh bouillon. Impedance measurement with BacTrac was done over 20 h.

It could be shown that the addition of bismuth in the silicon polymer formulation leads to an inhibition/delay of proliferation as already shown for the PUR/SMA-bismuth formulations.

Example 11

ICG Levels of the Silicon-Bismuth Films

Example 11 was performed on the silicon-bismuth films prepared in Example 9 in accordance with Example 3.

The results of the investigated films (prepared according to Example 9) are shown in Table 7.

TABLE 7

ICG levels of silicon-bismuth films (Example 9)

| Film | ICG (%) |
|---|---|
| Silicon (without bismuth) | 0.3 |
| Silicon 0.06% bismuth | 0 |
| Silicon 0.2% bismuth | 99.6 |

Films (5-20 μm thick) with a triphenylbismuth dichloride concentration of 0.5 weight %, corresponding to 0.2 weight % bismuth are toxic in the ICG assay. Silicon films without bismuth and films with 0.15 weight % triphenylbismuth dichloride, corresponding to 0.06% bismuth show no inhibition of cell growth.

The invention claimed is:
1. A biocompatible polymer composition comprising a bismuth complex, a polyurethane film forming polymer, and a polylactone-polydimethyl siloxane-polylactone triblock copolymer with mono, bi, or multiple end-groups reactive with the polyurethane polymer, wherein the bismuth complex is incorporated into the composition at 0.03% to 0.5% by weight bismuth and is at least one of ammonium bismuth citrate, bismuth(III)oxide, bismuth(III)gallate hydrate, bismuth citrate, bismuth(III)oxychloride, bismuth(III)tetramethylheptanedionate, bismuth(III)hexafluoracetonate, bis- muth(III)subsalicylate, triphenylbismuth, bismuth(III) ciprofloxacin, bismuth(III)chloride, triphenylbismuth dichloride, triphenylbismuth carbonate, triphenylbismuth di hydroxide, triphenylbismuth dinitrate, triphenylbismuth disalicylate, triphenylbismuthine, triphenylbismuth bis(2-chloroacetate), triphenylbismuth bis(4-aminobenzoate), bis(acetato-O)triphenylbismuth, dibromotriphenylbismuth, or difluorotriphenylbismuth.

2. The biocompatible polymer composition according to claim 1, wherein said polymer composition further comprises nano-particles, which comprise the bismuth complex.

3. The biocompatible polymer composition according to claim 1, wherein the bismuth complex is triphenylbismuth or triphenylbismuth dichloride.

4. A method of making a biocompatible polymer composition comprising incorporating a bismuth complex into a polymer composition comprising a polyurethane film forming polymer and a polylactone-polydimethyl siloxane-polylactone triblock copolymer comprising mono, bi, or multiple end-groups reactive with the polyurethane polymer, wherein the bismuth complex is present in an amount from 0.03% to 0.5% by weight bismuth and is at least one of ammonium bismuth citrate, bismuth(III)oxide, bismuth(III)gallate hydrate, bismuth citrate, bismuth(III)oxychloride, bismuth(III)tetramethylheptanedionate, bismuth(III)hexafluoracetonate, bismuth(III)subsalicylate, triphenylbismuth, bismuth(III)ciprofloxacin, bismuth(III)chloride, triphenylbismuth dichloride, triphenylbismuth carbonate, triphenylbismuth dihydroxide, triphenylbismuth dinitrate, triphenylbismuth disalicylate, triphenylbismuthine, triphenylbismuth bis(2-chloroacetate), triphenylbismuth bis(4-aminobenzoate), bis(acetato-O)triphenylbismuth, dibromotriphenylbismuth, or difluorotriphenylbismuth.

5. The method of claim 4, wherein nano-particles comprising the bismuth complex are incorporated into the polymer composition.

6. The method of claim 4 wherein the bismuth complex is triphenylbismuth dichloride or triphenylbismuth dichloride.

7. A method of making a medical device comprising
preparing a polymer composition by dissolving a bismuth complex, a polyurethane film forming polymer, and a polylactone-polydimethyl siloxane-polylactone triblock copolymer comprising mono, bi, or multiple end-groups reactive with the polyurethane polymer, in a solvent, wherein the bismuth complex is present in an amount from 0.03% to 0.5% by weight bismuth and is at least one of ammonium bismuth citrate, bismuth(III) oxide, bismuth(III)gallate hydrate, bismuth citrate, bismuth(III)oxychloride, bismuth(III)tetramethylheptanedionate, bismuth(III)hexafluoracetonate, bismuth(III)subsalicylate, triphenylbismuth, bismuth(III) ciprofloxacin, bismuth(III)chloride, triphenylbismuth dichloride, triphenylbismuth carbonate, triphenylbismuth di hydroxide, triphenylbismuth dinitrate, triphenylbismuth disalicylate, triphenylbismuthine, triphenylbismuth bis(2-chloroacetate), triphenylbismuth bis(4-aminobenzoate), bis(acetato-O)triphenylbismuth, dibromotriphenylbismuth, or difluorotriphenylbismuth
incubating the solution formed under conditions to allow the components of the solution to react with one another, and
coating a surface of a medical device under conditions that allow the solvent to evaporate.

8. The method of claim 7 wherein the bismuth complex is triphenylbismuth dichloride.

9. A medical device comprising a biocompatible surface for contacting at least one of blood, tissue, skin, epithelial layers, and wounds, at least a portion of the surface of said medical device being coated with a polymer composition film comprising at least one of triphenylbismuth and triphenylbismuth dichloride in an amount ranging from 0.03 to 0.08% by weight bismuth of the polymer composition, the polymer composition further comprising a polyurethane film-forming polymer component and a hydrophobic polymer block having reactive end-groups, the hydrophobic polymer block being a polylactone-polydimethyl siloxane-polylactone triblock copolymer comprising mono, bi or multiple endgroups reactive with the polyurethane polymer, wherein no triphenylbismuth and/or triphenylbismuth dichloride is released from the film into blood when the film is in contact with blood.

10. The medical device according to claim 9 having a multilayer coating of said polymer composition.

11. The method according to claim 7, wherein the coating forms a film on the surface by spreading.

12. The medical device according to claim 9, wherein the entire surface of the device is covered by one or more films of the polymer composition.

* * * * *